US006720049B2

(12) United States Patent
DiMaio, Jr.

(10) Patent No.: US 6,720,049 B2
(45) Date of Patent: Apr. 13, 2004

(54) THIN-WALLED POLYURETHANE ARTICLES

(75) Inventor: William G. DiMaio, Jr., Boothwyn, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 64 days.

(21) Appl. No.: 10/165,660

(22) Filed: Jun. 7, 2002

(65) Prior Publication Data

US 2003/0228477 A1 Dec. 11, 2003

(51) Int. Cl.⁷ .............................. B29D 22/00
(52) U.S. Cl. ............. 428/35.7; 428/36.5; 428/323; 428/324; 428/325; 428/328; 428/331; 428/423.1; 428/423.3
(58) Field of Search ............... 428/323, 324, 428/325, 328, 331, 35.7, 36.5, 423.1, 423.3

(56) References Cited

U.S. PATENT DOCUMENTS

| | | |
|---|---|---|
| 2,814,834 A | 12/1957 | Hess et al. |
| 3,524,753 A | 8/1970 | Sharp |
| 3,553,308 A | 1/1971 | Kobayashi et al. |
| 3,622,526 A | 11/1971 | Zorn et al. |
| 3,634,184 A * | 1/1972 | Wang ............... 442/64 |
| 3,786,580 A * | 1/1974 | Dalebout ............... 36/93 |
| 3,832,214 A | 8/1974 | Wang |
| 4,341,689 A | 7/1982 | Doshi et al. |
| 4,521,465 A | 6/1985 | Schroer et al. |
| 4,657,613 A | 4/1987 | Thoma et al. |
| 5,132,129 A | 7/1992 | Potter et al. |
| 5,391,343 A | 2/1995 | Dreibelbis et al. |
| 5,395,666 A * | 3/1995 | Brindle ............... 428/36.4 |
| 5,728,340 A | 3/1998 | Dreibelbis et al. |
| 6,016,570 A | 1/2000 | Vande Pol et al. |
| 6,027,803 A | 2/2000 | Jacobson et al. |
| 6,203,901 B1 | 3/2001 | Kosinski et al. |
| 2001/0014796 A1 | 8/2001 | Mizutani et al. |

FOREIGN PATENT DOCUMENTS

| | | |
|---|---|---|
| EP | 1125978 A1 | 8/2001 |
| FR | 2745817 A1 | 9/1997 |
| JP | 58186402 A | 10/1983 |
| JP | 95048779 A | 2/1995 |
| JP | 95097461 A | 4/1995 |
| JP | 11-140715 A | 5/1999 |
| SU | 1509832 A1 | 9/1989 |
| WO | WO 9415654 A1 | 7/1994 |
| WO | WO96/08353 A1 | 3/1996 |
| WO | WO 9918156 A1 | 4/1999 |
| WO | WO99/47127 A1 | 9/1999 |

OTHER PUBLICATIONS

Database WPI, Section Ch, Week 199931, Derwent Publications Ltd., London, GB; Class A25, AN 1999–367536, XP002253771.

* cited by examiner

*Primary Examiner*—Leszek Kiliman
(74) *Attorney, Agent, or Firm*—Robert B. Furr, Jr.

(57) ABSTRACT

This invention relates to low-tack thin-walled articles comprising a polyurethane elastomer, for example surgical gloves, clean-room gloves, condoms, and the like. More particularly, the invention relates to such elastomeric articles containing specific amounts of molecular sieve.

8 Claims, No Drawings

THIN-WALLED POLYURETHANE ARTICLES

BACKGROUND OF THE INVENTION

1. Field of the Invention

This invention relates to low-tack thin-walled articles comprising a polyurethane elastomer, for example surgical gloves, clean-room gloves, condoms, and the like. More particularly, the invention relates to such elastomeric articles containing specific amounts of molecular sieve.

2. Description of Background Art

Elastomeric gloves are known for use in sterile, surgical, and chemical environments. United States Patents U.S. Pat. No. 2,814,834 (Hess et al.), U.S. Pat. No. 3,553,308 (Kobayashi et al.), and U.S. Pat. No. 5,132,129 (Potter et al.) disclose "reaction dipping" methods for making gloves. United States Patents U.S. Pat. No. 5,391,343 (Dreibelbis et al.) and U.S. Pat. No. 5,728,340 (Dreibelbis et al.) described processes for making polyurethane thin-walled articles, such as gloves and condoms, which have superior mechanical properties, for example low set and high resistance to tear and puncture.

A problem characteristic of elastomeric thin-walled articles like gloves is surface tack, which can result in difficulty removing a glove from the mandrel during manufacture or from its package, and/or difficulty in donning a glove. United States Patent U.S. Pat. No. 6,016,570 (Vande Pol et al.) discloses the use of powder and lubricant additives and of contact-reducing textures formed by intermittent spray coating (optionally containing fillers to reduce droplet size) to control tack of vinyl gloves. However, lubricants can contaminate clean rooms and operating rooms, and surface textures can reduce tactility. Several disclosures have been made of inorganic particulates in polymers: in United States Patents U.S. Pat. No. 3,832,214 (Wang) and U.S. Pat. No. 3,622,526 (Zorn et al., directed to porous coagulated coatings for simulated leather), U.S. Pat. No. 4,521,465 (Schreor et al., directed to coated textiles as pipe liners), U.S. Pat. No. 6,203,901 (Kosinski et al., directed to clay in fibers and films), U.S. Pat. No. 6,027,803 (Jacobson et al., directed to barium sulfate in fibers), and European Patent Application EP1125978 (Roberts, directed to clay in latices). However, reduced tack polyurethane elastomeric thin-walled articles are still needed.

SUMMARY OF THE INVENTION

The present invention provides a thin-walled article comprising at least one surface layer of: a polyurethane elastomer; and about 20 to 40 weight percent, based on the weight of the layer, of a molecular sieve having a mean particle size of about 1 to 15 microns and less than 1 weight percent, based on weight of molecular sieve, of particle size greater than about 40 microns.

DETAILED DESCRIPTION

It has now been unexpectedly found that thin-walled articles containing certain amounts of molecular sieve have an unexpected combination of very low tack, low porosity, reduced set and stress, smooth hand, no particulate visible to the unaided eye, and only slightly opaque appearance. The low tack is advantageous for removing the article from a package and for donning, the low porosity for good barrier protection in clean room and medical environments, the reduced set and stress for better shape retention and improved comfort, and the tactile and visual properties for good aesthetics.

The term "thin-walled", as used herein, refers to a thickness of no greater than about 0.18 millimeters. The article can be said to have an inner surface and an outer surface, preferably identified in the configuration in which the article is to be used. "Polyurethane" refers to a long-chain synthetic polymer comprising alternating "soft segments" comprising primarily polyester, polyether, or polycarbonate and "hard segments" derived from the reaction of a diisocyanate and a difunctional chain extender. "Elastomer" means a polymer which, free of diluents, retracts to less than 1.5 times its original length within one minute after being stretched at room temperature to twice its original length and held for one minute before release. "Molecular sieve" means a crystalline inorganic material having pores, cavities, or other interstices which are uniformly on the order of Angstroms in size and includes synthetic and natural zeolites, which can be alumino-silicates, titano-silicates, and the like.

The thin-walled article of the invention comprises at least one surface layer of a polyurethane elastomer and about 20 to 40 wt % (preferably about 25 to 35 wt %), based on the weight of the layer, of a molecular sieve having a mean particle size of about 1 to 15 microns and less than about 1 wt %, based on weight of molecular sieve, of particle size greater than about 40 microns. The article can have a stress at 100% extension of no greater than about 200 psi (1.4 megaPascals), a "calculated water vapor transmission rate" of less than about 50 g/hr/m$^2$ (preferably less than about 20 g/hr/m$^2$), calculated for an 0.1 mm thick sample, and a percent set of less than about 25%.

Elastomeric polyurethanes useful in this invention can be prepared by reacting a polymeric glycol with a diisocyanate to form an isocyanate-terminated prepolymer (a "capped glycol"), preferably having an isocyanate (NCO) end-group concentration in the range of about 1.4 to 2.0%. The capped glycol can be dissolved in a suitable solvent, and then reacting the capped glycol with a difunctional chain extender having active hydrogen atoms. Suitable solvents for preparing solutions of such polymers are amide solvents such as dimethylacetamide ("DMAc"), dimethylformamide, and N-methylpyrrolidone, but other solvents such as dimethylsulfoxide and tetramethylurea can also be used.

Polymeric glycols used in the preparation of the elastomeric polyurethanes include polyether glycols, polyester glycols, polycarbonate glycols and copolymers thereof. Examples of such glycols include poly(ethyleneether) glycol, poly(trimethyleneether) glycol, poly(tetramethyleneether) glycol, poly(tetramethylene-co-2-methyltetramethyleneether) glycol, poly(ethylene-co-butylene adipate) glycol, poly(2,2-dimethyl-1,3-propylene dodecanedioate) glycol, poly(3-methyl-1,5-pentamethylene dodecanedioate) glycol, poly(pentane-1,5-carbonate) glycol, and poly(hexane-1,6-carbonate) glycol. Polyester glycols having a number average molecular weight of about 3,000 to 6,000 are preferred. Polyester glycols derived from the reaction of adipic acid with a mixture of ethylene glycol and 1,4-butanediol (mole ratio of 30:70 to 75:25) are more preferred.

Useful diisocyanates include 1-isocyanato-4-[(4'-isocyanatophenyl)methyl]benzene (preferred), 1-isocyanato-2-[(4'-isocyanato-phenyl)methyl]benzene, isophorone diisocyanate, 1,6-hexanediisocyanate, 2,4-tolylene diisocyanate, and mixtures thereof.

The chain extender can be a diol, an aminoalcohol, or a diamine. Useful diols include ethylene glycol, 1,3-trimethylene glycol, 1,4-butanediol, and mixtures thereof. When the chain extender is a diol, the polyurethane can be prepared using the two-step prepolymer method described hereinabove or using a one-step method in which the ingredients are mixed together at substantially the same time. Useful diamines include ethylene diamine (preferred), 1,2-propanediamine, 2-methyl-1,5-pentanediamine, 1,3-diaminopentane, 1,4-cyclohexane-diamine, 1,3-cyclohexanediamine, and mixtures thereof. When the chain extender is a diamine, the two-step, prepolymer polymerization method is generally used. Monofunctional amine chain terminators such as diethyl amine, butylamine, cyclohexylamine, and the like can be added to control the molecular weight of the polymer, and small amounts of trifunctional ingredients such as diethylenetriamine can be added for solution viscosity control.

Typically, the solution of polyurethane can have a falling ball viscosity of about 25 to 125 poise and a polyurethane concentration of about 12 to 20 wt %, based on the total weight of the solution.

The molecular sieve can be mixed directly into the polyurethane solution, or optionally prepared first as a concentrated slurry or masterbatch which can then be added to the main polyurethane solution. The molecular sieve can generally be used as-received from the supplier; however if it has been exposed to water or water vapor, it can be advantageous to dry it before use to reduce the risk of increased gel formation in the dipping mixture, but such a problem was not observed in the present work. The addition of the molecular sieve can result in increased viscosity of the mixture compared to the polyurethane solution, but this can be easily reduced to about that of the polyurethane solution by adding more solvent.

If desired, other additives such as UV screeners, antioxidants, and the like can be added to the dipping mixture, provided such additives do not detract from the benefits of the invention. However, for clean room and medical use, it is preferred that no such additives be used in order to reduce the release of contaminants into such critical environments.

The thin-walled article can be prepared as follows. The dipping mixture of polyurethane and molecular sieve, which can be prepared as described hereinabove and maintained at about 20° C. to 30° C., can be degassed by subjecting it to vacuum for a few minutes to remove entrapped and/or dissolved air. A ceramic or aluminum mandrel of the desired size and shape, optionally heated and having a matte finish, can then be dipped into the degassed solution, preferably at an angle of about 80° to almost 90° with, in the case of a glove mandrel, the fingers entering the mixture first and the palm facing upward. The mandrel can be kept in the mixture for about 5 to 30 seconds, removed over a period of 10 to 15 seconds, and allowed to drain for about 1 to 5 minutes. The coated mandrel can then be inverted, dried for a sufficient time and at a sufficient temperature to remove the solvent, and allowed to cool. The glove can then be stripped from the mandrel by eversion. Dipping the coated mandrel into water optionally containing surfactants can assist in stripping the article from the mandrel.

The thin-walled article comprises at least one surface layer of polyurethane elastomer containing molecular sieve. Other layers can be applied by carrying out other dipping steps, either before or after applying the layer containing molecular sieve. For reduced tack, at least one layer containing molecular sieve is a surface layer of the article. However, thin layers, for example comprising microbicide, spermicide, and the like, can be applied over a molecular-sieve containing surface layer, provided the benefits of the invention are not compromised. When a plurality of dipping steps is carried out, the mandrel can be pre-heated, for example to about 85° C., before the first dip to help avoid nonuniformities in the thin-walled article. Optionally, a first dipping step can be into a polyurethane solution substantially free of molecular sieve, and a second dipping step can be into the polyurethane/molecular sieve mixture, so that only one layer of the article contains the molecular sieve. Upon removal with eversion from a matte-finished mandrel, the thin-walled article can then have a molecular sieve-containing polyurethane elastomer inner surface layer for easy donning and a polyurethane elastomer outer, second, layer substantially free of molecular sieve but having a matte finish for easy removal from a package. If desired, such later dipping step(s) can also be made to limited, appropriate depths so that the polyurethane/molecular sieve mixture is applied only to pre-selected portions of the coated mandrel, for example to add thickness and reduce tack only in the finger or finger-and-palm portions of a glove.

Although release agents such as perfluoropolymers or silicone oil can optionally be applied to the mandrel before dipping it into the mixture or added directly to the dipping mixture, such agents have not typically been found necessary in the inventive process. This is an advantage for clean room and medical use, because release agents are potentially extractable.

In the Examples, the particulate additives were used as received from the supplier. The polyurethane solution viscosity was determined in accordance with the general method of ASTM D1343-69 with a Model DV-8 Falling Ball Viscometer, (sold by Duratech Corp., Waynesboro, Va.), operated at 40° C.

Qualitative evaluation of film tack was carried out by doubling a film on itself, pressing the folded film together, and gently pulling the folded parts away from each other. "Surface feel" and particle shedding were performed by running a hand lightly along the surfaces of the films, and, in the latter test, rubbing the fingers together to see if a residue was evident. Qualitative visual observations were made on the films' light transmission, visibility of particulate matter, and variation in film thickness due to particulate agglomeration.

Water vapor transmission rates, used as a guide to porosity and barrier properties, were determined according to the method of ASTM E96-94, "Standard Test Method for Water Vapor Transmission of Materials, Water Method". In this test, a 1.5 mil (0.038 mm) thick film sample was clamped without stretching to a flanged aluminum test cup having a mouth area of 31.7 cm$^2$ and containing 1.5 cm of distilled water whose surface was 19 mm below the sample. The test assembly was weighed and then placed in a test chamber held at 24° C. and 55% relative humidity and provided with an air flow of 2.8 m/s directed across the surface of the sample. After 24 hours, the test assembly was again weighed, and the loss of water and the water vapor transmission rate were calculated. The test was performed on six samples, and the average was recorded. For convenience, calculated water vapor transmission rates are also reported herein as reduced to those of an article having a thickness of 0.1 mm.

Mechanical properties were determined generally according to ASTM D412-98A (Standard Test Method for Vulcanized Rubber and Thermoplastic Elastomers—Tension), modified for cyclic extension of the film. In this test, a film sample 2 inches (5.1 cm) long, 0.5 inches (1.3 cm) wide and 2.8 mils (0.07 mm) thick was subjected to five 0–300% strain cycles at a constant elongation rate of 20 inches (51 cm) per minute. On the fifth unload cycle, the stress was determined at 100% extension and reported in psi and megaPascals, and the percent set was calculated as the extension at which the measured stress returned substantially to zero, according to the following equation:

% Set=$100(L_a-L_b)/L_b$, wherein $L_b$ and $L_a$ are respectively the film length, when held without tension, before and after the five elongation/relaxation cycles.

EXAMPLES

Example 1

A polyurethaneurea was prepared by reacting a 3400 number-average molecular weight polyester glycol (the reaction product of a 60/40 mole ratio mixture of ethylene glycol and 1,4-butanediol with adipic acid) with 1-isocyanato4-[(4-isocyanatophenyl)methyl]benzene (1.80% NCO, mole ratio of diisocyanate to polymeric glycol 1.83:1) to form an isocyanate-terminated prepolymer. The prepolymer was dissolved in DMAc and then chain-extended and -terminated with a mixture of ethylene diamine and cyclohexylamine to form a 17 wt % polyurethane solution in 25 DMAc. The solution viscosity was 115 poise. Titanium dioxide (Ti-Pure® R-706, a registered trademark of E. I. du Pont de Nemours and Company) and a molecular sieve having an 8 micron mean particle size and less than 1 wt % of a particle size above 18 microns (Sylosiv® A-3, W. R. Grace arid Company) were mixed into the polyurethane solution so that the final mixture contained 2 wt % of titanium dioxide and 30 wt % of molecular sieve, based on total solids. The viscosity of the resulting mixture was adjusted with additional DMAc. A film ("Sample 1") 1.5 mil (0.038 mm) thick was cast from the polyurethane/molecular sieve mixture with a doctor knife onto polyester film, dried at 80° C.–100° C. for 20–60 minutes, carefully peeled from the polyester film, and evaluated visually and by hand.

Similar films were cast from mixtures of the same polyurethane and titanium dioxide with no other added particulate (Comparison Sample 1), with added kaolin clay powder (VWR Company, 5 micron mean particle size, 0.8 to 26 micron size range) (Comparison Sample 2), with added silica gel (EM Science, 48 micron mean particle size, 7 to 160 micron size range, 90% between 40 and 63 microns) (Comparison Sample 3), with added Zonyl® Fluoroadditive MP1000 low molecular weight polytetrafluoroethylene powder (a registered trademark of E. I. du Pont de Nemours and Company, 9 micron mean particle size, 1 to 36 micron size range) (Comparison Sample 4), and with added cornstarch (ARGO, Best Foods, 13 microns mean particle size, 1 to 35 micron size range) (Comparison Sample 5). Table I presents the results.

TABLE I

| Sample | Film Description | Tack | Surface Feel | Light Transmission | Visible Particulate | Thickness Variation | Particle Shedding |
|---|---|---|---|---|---|---|---|
| 1 | 70/30 wt % PU/Molecular Sieve | None | Smooth | Slightly opaque | No | Small | No |
| Comp. 1 | PU | High | Smooth | Translucent | No | Small | No |
| Comp. 2 | 70/30 wt % PU/Kaolin Clay Powder | None | Slightly textured | Yellow discoloration | Yes | Moderate | No |
| Comp. 3 | 70/30 wt % PU/Silica Gel | None | Rough | Slightly opaque | Yes | Large | No |
| Comp. 4 | 70/30 wt % PU/Zonyl® MP1000 Powder | None | Rough | Slightly opaque | Yes | Large | No |
| Comp. 5 | 70/30 wt % PU/Cornstarch | None | Nearly smooth | Slightly opaque | Yes | Small | Yes |

As shown in Table 1, Sample 1, with 30 wt % molecular sieve based on is total solids, exhibited no tack or visible particulate or apparent particle shedding, and had a smooth surface feel, only small variation in thickness, and slight increase in opacity. In contrast, all the Comparison Samples were deficient with respect to one or more such attributes.

Example 2

Sample 1 and Comparison Sample 1 were evaluated for barrier properties by applying ASTM E96-94. Sample 1, containing 30 wt % molecular sieve based on total film weight, was found to have a water vapor transmission rate of 638 g/m$^2$ over a 24 hour period (calculated to be 10 g/hr/m$^2$ for an 0.1 mm thick film). That represented only a modest increase over the rate of 514 g/m$^2$ over a 24 hour period (calculated to be 8 g/hr/m$^2$ for an 0.1 mm thick film) for Comparison Sample 1, containing no molecular sieve. Such a low water vapor transmission rate is indicative of good barrier properties.

Example 3

To determine the effect of added molecular sieve on mechanical properties, Sample 2 was cast onto a polyester film from the same polyurethane/molecular sieve composition as was used for Sample 1 and dried. The resulting 2.8 mil (0.07 mm) thick polyurethane film, still on the polyester film, was cut to an appropriate size, the polyurethane film was carefully peeled from the polyester film, and the polyurethane's properties were determined with an Instron® tensile tester. Comparison Sample 6 was cast from the same polyurethane solution composition as Comparison Sample 1 and similarly prepared for testing. The stress results were, for Sample 2, 144 psi (0.99 megapascals) and for Comparison Sample 6, 291 psi (2.00 megapascals) stress at 100% extension, showing a beneficial reduction in stress under typical wearing extension. Sample 2 also exhibited advantageously lower set (22%) than did Comparison Sample 6 (27%).

What is claimed is:

1. A thin-walled article comprising at least one surface layer of:

a polyurethane elastomer; and about 20 to 40 weight percent, based on the weight of the layer, of a molecular sieve having a mean particle size of about 1 to 15 microns and less than 1 weight percent, based on weight of molecular sieve, of particle size greater than about 40 microns.

2. The thin-walled article of claim 1 having a calculated water vapor transmission rate of less than about 50 g/hr/m$^2$ and a stress at 100% extension of no greater than about 1.4 megaPascals.

3. The thin-walled article of claim 1 wherein the polyurethane comprises the reaction product of a polyester glycol, a diisocyanate, and a diamine chain extender.

4. The thin-walled article of claim 2 wherein the molecular sieve is present at about 25 to 35 weight percent, based on the weight of the article.

5. The thin-walled article of claim 1 having a calculated water vapor transmission rate of less than about 20 g/hr/m$^2$.

6. The thin-walled article of claim 1 further comprising a second layer of polyurethane elastomer substantially free of molecular sieve.

7. The thin-walled article of claim 6 wherein the layer containing molecular sieve is an inner surface layer and the second layer is an outer layer of the article.

8. The thin-walled article of claim 3 having a percent set of less than about 25%.

* * * * *